(12) United States Patent
Pierce

(10) Patent No.: US 7,373,254 B2
(45) Date of Patent: May 13, 2008

(54) DISINFESTATION OF MEDICAL IMPLANTS WITH RADIATION

(75) Inventor: Brian N. Pierce, Hamilton City, CA (US)

(73) Assignee: Advanced Light Technology, LLC, Chico, CA (US)

( * ) Notice: Subject to any disclaimer, the term of this patent is extended or adjusted under 35 U.S.C. 154(b) by 135 days.

(21) Appl. No.: 10/138,350

(22) Filed: May 3, 2002

(65) Prior Publication Data

US 2003/0027186 A1 Feb. 6, 2003

Related U.S. Application Data

(60) Provisional application No. 60/288,505, filed on May 3, 2001.

(51) Int. Cl.
| | |
|---|---|
| G01N 33/48 | (2006.01) |
| A61N 5/06 | (2006.01) |
| A61B 18/18 | (2006.01) |
| A61L 2/00 | (2006.01) |
| B01J 19/12 | (2006.01) |

(52) U.S. Cl. .................. 702/19; 702/20; 607/89; 606/3; 606/9; 606/18; 422/22; 204/157.61

(58) Field of Classification Search .................. 702/19
See application file for complete search history.

(56) References Cited

U.S. PATENT DOCUMENTS

| | | | |
|---|---|---|---|
| 3,941,670 A | 3/1976 | Pratt, Jr. | |
| 4,170,997 A | 10/1979 | Pinnow et al. | |
| 4,469,098 A | 9/1984 | Davi | |
| 4,640,283 A | 2/1987 | Sawa et al. | |
| 4,672,969 A | 6/1987 | Dew | |
| 4,792,341 A | 12/1988 | Kozikowski et al. | |
| 4,836,203 A | 6/1989 | Müller et al. | |
| 4,880,512 A | 11/1989 | Cornelius et al. | |
| 4,920,978 A | 5/1990 | Colvin | |
| 4,926,861 A | 5/1990 | Fenyo et al. | |
| 5,186,181 A | 2/1993 | Franconi et al. | |
| 5,197,470 A | 3/1993 | Helfer et al. | |
| 5,707,401 A | 1/1998 | Talmore | |
| 5,820,820 A | 10/1998 | Pierce | |
| 5,881,534 A | 3/1999 | Ahlqvist et al. | |
| 5,993,442 A | 11/1999 | Omori | |
| 6,011,889 A | 1/2000 | Daniel et al. | |
| 6,030,653 A | 2/2000 | Rosenthal | |
| 6,035,246 A | 3/2000 | Wagner | |
| 6,090,102 A | 7/2000 | Telfair et al. | |
| 6,106,521 A | 8/2000 | Blewett et al. | |
| 6,110,195 A | 8/2000 | Xie et al. | |
| 6,162,213 A | 12/2000 | Stewart | |
| 6,267,779 B1 | 7/2001 | Gerdes | |
| 6,268,200 B1 | 7/2001 | Tucker et al. | |
| 2002/0002391 A1 | 1/2002 | Gerdes | |

FOREIGN PATENT DOCUMENTS

| | | |
|---|---|---|
| CA | 2326120 A1 | 10/1999 |
| DE | 41 19 149 | 11/1992 |
| WO | WO 97/02862 A1 | 1/1997 |

OTHER PUBLICATIONS

Ahn CY, Ko CY, Wagar EA, Wong RS, Shaw WW., Microbial evaluation: 139 implants removed from symptomatic patients. Plast Reconstr Surg. Dec. 1996;98(7):1225-9. (abstract only).*
Roberts et al. Cold pasteurization of food by irradiation. URL=http://www.ext.vt.edu/pubs/foods/458-300/458-300.html.*
Ter-Mikirtychev, Diode-pumped Li:F(2+) Color Center Laser Tunnable in 880-995-nm Region at Room Temperature, IEEE Photonics Technology Letters, 1998, p. 1295-1397.*
Browne M., Schaum's Outline of Theory and Problems of Physics for Engineering and Science, p. iii and 209, 1999.*
Ahn et al., Ahn et al., Plast. Reconstr. Surg. Dec. 1996, 98(7):1225-9 (full text), abstract has been provided.*
Webb et al., Food Irradiation, Kansas Sate University Agricultural Experiment Station and Coooperative Extension Service, Feb. 2000.*
Roberts et al. Cold pasteurization of food by irradiation 1998. URL=http://www.ext.vt.edu/pubs/foods/458-300/458-300.html.*
J. Econ. Entomology; 91:4, pp. 899-904; Mar. 1998; Dowell et al.
J. Econ. Entomology; 92:1, pp. 165-169; Sep. 1998; Dowell et al.
Dowell et al., *Identifying Stored-Grain Insects Using Near-Infrared Spectroscopy*, J. Econ. Entomology, 92:1, pp. 165-169 (Feb. 1999).

* cited by examiner

*Primary Examiner*—Shubo (Joe) Zhou
(74) *Attorney, Agent, or Firm*—Townsend and Townsend and Crew LLP; Henry Heines

(57) ABSTRACT

The present invention relates to the process of selectively exposing matter to a specific wavelength of electromagnetic energy in sufficient flux density per wavelength to cause or promote a desired effect. The process includes, but is not limited to, destroying, disinfecting, denaturing, disinfesting, disrupting, or dehydration of one or more of the substances present. More specifically, present invention relates to subjecting matter, which may contain a mixture of substances, to electromagnetic energy, in concurrence with its spectral properties to exploit the spectral differences within the substance or within a mixture of substances. Energies are applied to cause wavelength-dependent reactions resulting from differential absorption; this additional applied energy manifests itself in changes, or quantum transitions, in the vibrational, rotational, magnetic, and electronic states of the molecules. Generally, the process utilizes wavelengths from about one light second to about ten electron volts, or wavelengths with energy levels less than that of ionization.

6 Claims, 7 Drawing Sheets

DISINFESTATION OF MEDICAL IMPLANTS WITH RADIATION

RELATED APPLICATION

This application is based on copending U.S. Provisional Application Ser. No. 60/288,505, entitled "Differential Photochemical Processing," which was filed on May 3, 2001. The benefit of the filing date of this Provisional Application is claimed for this application.

BACKGROUND OF THE INVENTION

Many people are aware of the need to reduce the use of and reliance on synthetic chemicals and antibiotics, as well as pesticides and herbicides; it is clear that unless safe alternatives are brought forth, the implications for medicine, agriculture, and global society are immense. Each year, countless doses of antibiotics and other medicines are used in an attempt to control many different afflictions and infestations. Humans and crops are treated with countless chemicals and radiation; children afflicted with head lice are shampooed with insecticides. While these agents are effective against numerous illnesses and pests, their use has become increasingly of public concern because of the threat such chemicals pose to the environment and to human health.

Discovering that microbes—pathogens, bacteria, or pests have developed a resistance to chemicals, antibiotics, medicines, or pesticides isn't news anymore; agriculturists and physicians expect only five to ten years of effectiveness from a new chemical before the target pathogen or pest begins to show resistance and alternatives must be found. Many of the most effective pesticides and herbicides are now slated for elimination under the Food Quality Protection Act and the Clean Air Act. This legislation will begin to address environmental concerns, but the pending loss of these chemicals has renewed the sense of urgency felt by agriculturists worldwide for ways to maintain their economic viability and international trade status. Also many antibiotics are used incorrectly or incompletely diminishing their effectiveness.

Photochemical and photomechanical reactions are the two elements of this patent. Photochemical reaction is a reaction influenced or initiated by light, particularly ultraviolet light. Selective photochemical processing is a sophisticated pollution-free method of processing or treatment. Photomechanical reaction is a term we use to describe the molecular mechanical reactions resulting from exposure to Electromagnetic Energy (EME); the bending, stretching, rocking, rotation and vibrations are physical or mechanical actions. Explained in greater detail below. In the present invention selected wavelength(s) can be specifically designed for each application so that the light (EME) employed affects only the target or infestation, and not the human or agricultural product treated.

Host or product considered for treatment as well as the associated target or infestation are subjected to testing to determine spectral properties. Compiled spectra from host and target or infestation are compared; frequencies, which exhibit the highest, or sufficient differential absorption, are considered for use in processing. Frequencies considered are then evaluated for availability, power conversion efficiency, available flux density, band width of emission, efficiency after filtering or frequency modulation, and transparency of host at the considered wavelength.

When a wavelength has been selected, flux density tests are conducted. In all cases where the host is not expendable for testing, in vitro testing will be performed. In the case of a host for which it is not objectionable to damage the host (such as food items including grain or raw meat or fish, or paint, for example), samples of the host product are subjected to increasing intensities of the selected wavelength to the point when the host is determined to have suffered undesirable effects. The target or infestation is also treated in the same manner and monitored for kill or disruption of one or more metabolic functions. The difference in absorption is realized and perimeters for processing are then established. Process time is limited by several factors, the first being the magnitude of differential absorption. Host and related infestations with a high degree of differential absorption can have very short process times provided high intensity sources are available with narrow band emission at the desired wavelength. Host and related infestations with a low degree of differential absorption are preferably targeted at several differential sites with appropriate wavelengths. Multi-mode processing, or multiple wavelength treatment, can utilize any or all wavelengths that do not cause an undesirable effect in the host. Infestation proximity to host (whether the target is embedded in the host or located on the surface) is factored. If the infestation is embedded in the host, the host must have some degree of transparency at treatment wavelength to allow the energy to reach the infestation or the capacity to conduct or transmit the selected energy to the infestation location. If the infestation is located on the surface of the host, the host need only be a non-absorber or a reflector at the treatment wavelength. Surface infestation allows for many more wavelength possibilities, as most substances have fewer transparent wavelengths. Finally, the physical state of the product, and the method of conveying the product to the exposure site are considered. Examples of methods of conveying the product to the exposure site are a conveyor belt, a screw-conveyor, pneumatic conveyance, and a rotating drum.

BRIEF SUMMARY OF THE INVENTION

The present invention relates to the process of selectively exposing matter to specific wavelengths of electromagnetic (EM) energy in sufficient flux density per wavelength to cause or promote a desired effect. The process includes, but is not limited to, destroying, disinfecting, denaturing, disinfesting, disrupting, or dehydrating one or more of the substances present. More specifically, the present invention relates to subjecting matter, which may contain a mixture of substances, to electromagnetic energy in concurrence with its spectral properties to exploit the spectral differences within the substance or within a mixture of substances. Energies are applied to cause wavelength-dependent reactions resulting from differential absorption; this additional applied energy manifests itself in changes, or quantum transitions, in the vibrational, rotational, magnetic, and electronic states of the molecules. Generally, the process utilizes wavelengths from about one light second to about ten electron volts, or wavelengths with energy levels less than that of ionization.

The differential absorption process of the present invention has an advantage over chemicals due to the fact that pests or pathogens cannot become resistant to heat or to the absorption of electromagnetic (EM) energy. Additionally, the process does not require the time and expense it takes to register new chemicals or drugs, and good scale-up test results for implementation can be available. The frequencies used in the process do not have the ability to break chemical bonds. Preferably, frequencies applied have insufficient energy to break a chemical bond, and no ionizing energy is utilized. Chemical bonds may be disassociated, vibrated, rotated, etc., but not broken. The process does not have the ability to make a chemical change in a product; therefore, it is particularly useful for organic as well as commercial applications.

Scientists have used infrared (IR) spectroscopy for quantitative and qualitative analysis for decades with great refinements in recent years. IR spectroscopy can now detect pathogens in grain on conveyer lines, and newly developed IR monitoring systems are now in use for detecting insect infestations in grain bins. The process of the present invention not only detects, but also exploits the spectral differences of products and pests. The process uses electromagnetic (EM) energy to promote reactions in different types of matter through its unique effects on all different types of matter.

Desired Effect

Desired effect is a descriptive name assigned to a predetermined positive outcome or result, through the use of this process. To include, but is not limited to, destroying, disinfecting, denaturing, disinfesting, disrupting, dehydration, marking, Tagging, illuminating of one or more of the substances present. Illuminating a substance through a designed process that exposes matter to a specific wavelength of EME to cause it emit or re-emit energy to aid in identification or exclusion of a specific substance. Marking a substance is a desired effect where an infestation or undesirable element of the substance can be changed or excited so it can be referenced. Tagging or designating a target for the desired effect of attracting a chemical, catalyst, agent, nanobot, etc. Dehydration to selectively reduce the percentage of water or solvent present in host or some portion of the host. Disruption of a substance, to cause a process to be interrupted or physical property to be changed in such a manner to cause dysfunction. Disinfesting to rid host of some type of infestation through a selective process that will kill or dislodge or make an environment undesirable or intolerable for infestation. Denaturing to change a protein by heating it so that the original properties such as solubility are changed as a result of the protein's molecular structure being changed in some way, to use EME as a denaturant. Disinfect to sterilize a substance, to free it from living organisms by subjecting it to EME targeted to some substance to cause it to die.

DETAILED DESCRIPTION OF THE INVENTION

General Biology of Arthropods

Figure 1:
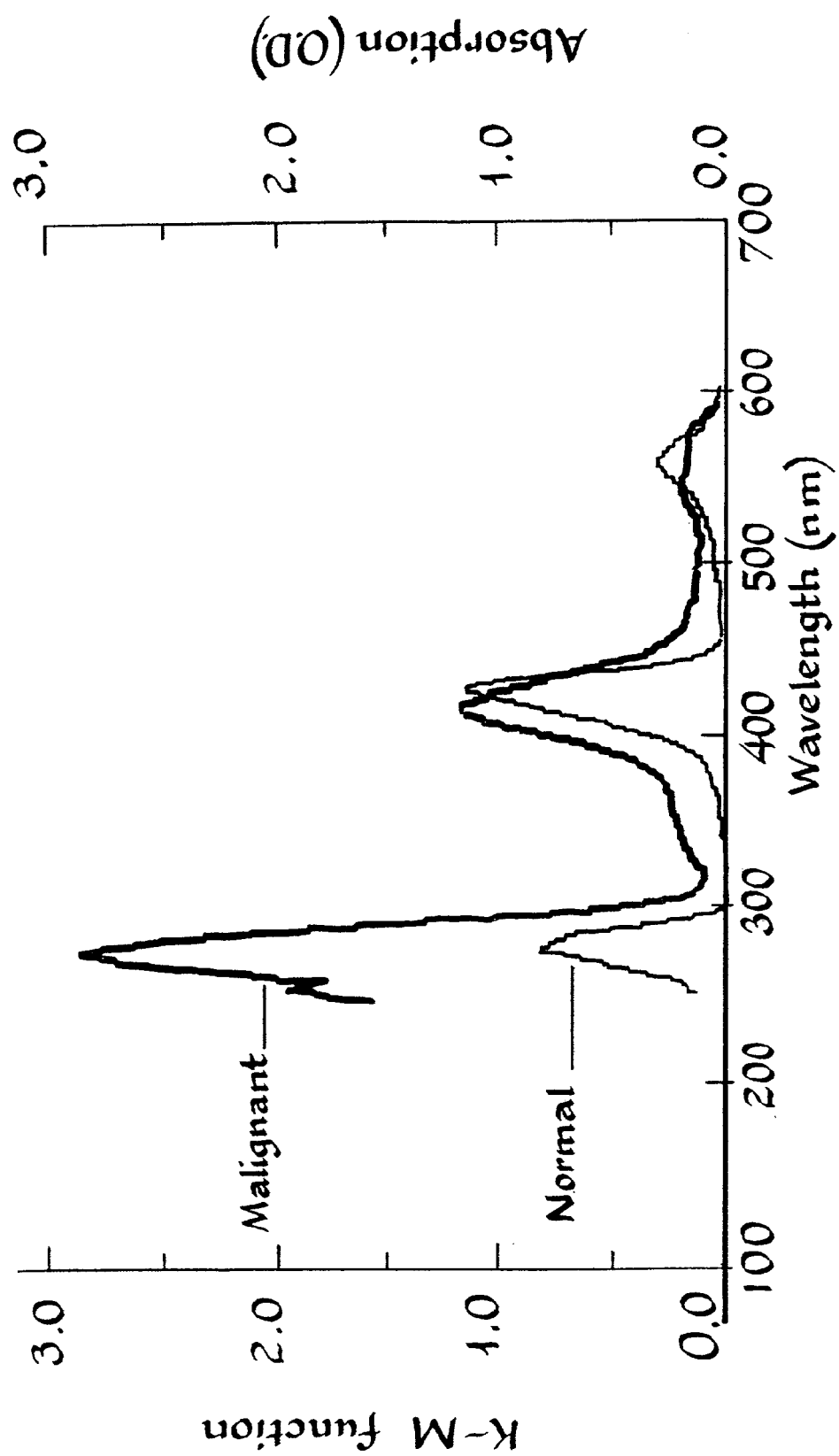
FIG. 1 Graph of absorption of DNA as a function of wavelength.
Figure 2:
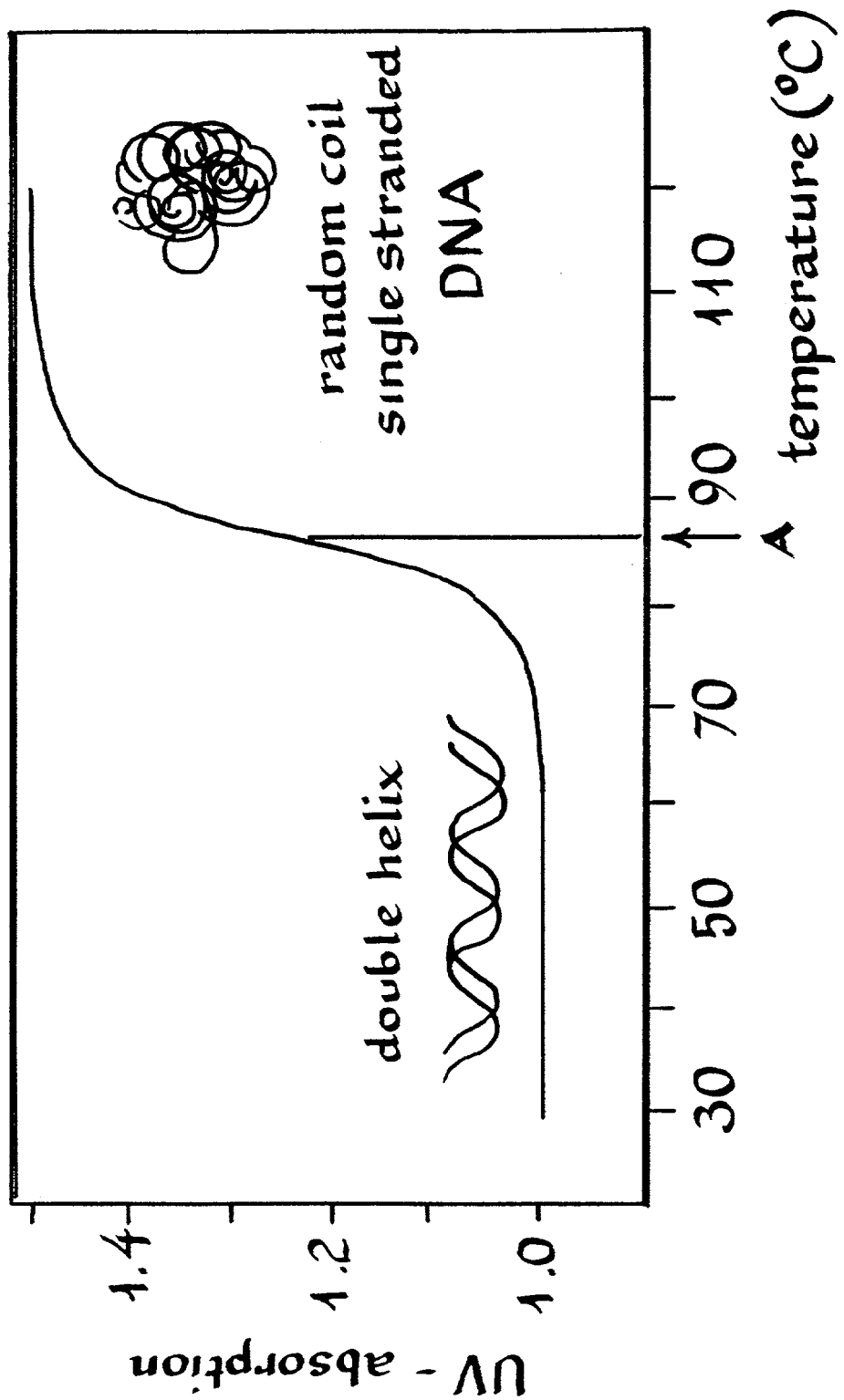
FIG. 2 Graph of absorption of DNA as a function of temperature illustrating melting temperature of double stranded DNA.

Arthropods are the most biologically successful organisms on earth in terms of the number of species, the sheer number of individuals, their total mass, and their pervasive occupation of all terrestrial habitats. The phylum *Arthropoda* is divided into three subphyla: *Chelicerata* (scorpions, spiders, ticks, mites), *Crustacea* (amphipods, isopods, land crabs), and *Uniramia* (insects, centipedes, millipedes). These subphyla contain roughly one million known species and are populated by an estimated quintillion (a billion billion) living individuals at any given time. In some of its aspects, this invention is useful in destroying arthropods in or on living tissue, including mammalian tissue and plant tissue.

One of the defining characteristics associated with the arthropods is the presence of a hardened exoskeleton or cuticle. The cuticle is a noncellular, multilayered membrane, which covers the single layer of epidermal cells from which it is excreted. While it varies in hardness, thickness, and composition across the array of arthropod species, the basic architecture and purpose of the cuticle are similar throughout the phylum. In general, the cuticle is divided into two strata: the epicuticle, the thin, outermost layer, and the underlying procuticle. The procuticle contains a sclerotized chitin-protein complex, which accounts for the shape and strength of the cuticle. (In contrast, the arthropodal membrane, which joins the sclerites and appendage segments, remains highly flexible and elastic because its proteins are not sclerotized.) The procuticle also contains some lipids and waxes, but not to the same degree as the epicuticle. In the procuticle, lipids and waxes are striated into various horizontal layers, including a superficially deposited layer on the cuticle surface. Despite its thinness (0.1-3 µm), the epicuticle, by virtue of its external location and the hydrophobic nature of its chemical components, provides the principle barrier to the diffusion of water across the arthropod cuticle.

Physiology

Extensive studies and frequent reviews (Blomquist and Jackson, 1979; Blomquist and Dillwith, 1985; Blomquist, 1987; Hadley, 1981; Lockey, 1985,1988; Renobles, 1991) have shown the epicuticle to be complex in nature. Its extracts typically contain straight chain and methyl-branched hydrocarbons (saturated and unsaturated), wax and sterol esters, acetate esters of keto-alcohols, ketones, alcohols, aldehydes, and free fatty acids.

In conjunction with its role as a water barrier for arthropods, the surface of the epicuticle is dominated by nonpolar constituents, such as straight-chain hydrocarbons (n-alkanes). These n-alkanes, seen in nearly every studied arthropod species, range in length from twenty to thirty-seven carbon atoms, with odd-numbered chains between the two limits. Branched hydrocarbons, including monomethyl-, dimethyl-, and more rarely, trimethylalkanes, usually accompany the n-alkanes. In addition, approximately 50% of the investigated species were found to have epicuticles containing olefins (unsaturated hydrocarbons) with one, two, and occasionally three degrees of unsaturation.

The epicuticle was also found to contain a full complement of oxygenated hydrocarbon derivatives; mixtures of saturated and unsaturated fatty acids having even chain lengths of ten to thirty-two carbons were common constituents, while free alcohols were found in less than half of the species analyzed. Wax esters were often extruded along with the hydrocarbons and ranged from simple to complex, depending upon the complexity of the alcohol and fatty acid components. These waxes were found to be the dominant surface lipids in black widow spiders, sand cockroaches, and scale insects.

Homeostasis

Water is essential to the arthropod's ability to maintain homeostasis; a dynamic balance of cellular conditions (temperature, pH, electrolyte concentrations, etc.) Water is especially important in maintaining a constant internal temperature, despite fluctuating environmental temperatures. Because of their small size and high surface area-to-volume ratios, arthropods gain heat rapidly from their environment. In order to offset this heat gain, they use evaporative cooling which requires arthropods to evaporate water (sweat) at a rate that is roughly proportional to their surface areas. The combination of heat gain and large surface area requires arthropods to devote a large portion of their small body volumes to water storage. Over time, arthropods developed the hydrophobic epicuticle, which facilitates both the storage of water and the regulation of its evaporation. Without the epicuticle, a terrestrial arthropod would be unable to maintain a constant internal temperature or sufficient water reserves and would rapidly desiccate.

Infrared Targeting of Insects

The cuticle is of supreme importance in the survival of insects, and since chitin is a major structural component of the cuticle, it is a desirable target site for selective pesticides.[i] However, the use of pesticides is not the only viable solution for insect control and eradication. The insect may be targeted at several regions of the body that relate to the cuticle, chitin, or other differential material, which is infrared or microwave responsive. For example, the sensory structures of insects, such as compound eyes, tympanic membranes, and antennae can be targeted, resulting in an insect that is blind, deaf, and unable to navigate or locate a mate.

Advantageously, it has been recognized that insects exposed to infrared sources have shown sensory difficulties without behavioral recognition of the light source. Upon exposure to a standard light source, insects respond and flee accordingly. Physiologically, some insects are virtually blind to red wavelengths of light but are able to see far into the ultraviolet.[ii] It has been inferred from these experimentally recorded phenomena by Menzel that no red (visible light) receptor exists in such insects (for example, Diptera).[iii,iv] This "red blindness" is a result of the absence of pigments which screen for longer wavelength radiation.[v] However, insects do possess a strong visual correlation between ultraviolet sensitive pigments and the spectral sensitivity maxima at 500, 450, or 350 nanometers; these pigments allow the insects to respond to the stray light spectral distribution of the sky.[vi,vii] Insects have a greater visual response to natural, stray light rather than narrow bandwidths of radiation: in other words, when exposed to stray light they run, hop, jump or fly away. Accordingly, infrared wavelengths remain transparent (non-visible) to arthropods. The arthropod cornea is constructed of transparent cuticle; therefore, the eyes of spiders and insects can be targeted by the process of the present invention.[viii,ix] Infrared penetration of the cornea (or tympanic membrane) would be able to disrupt visual (or auditory) function by the dehydration of the tissues, causing tissue damage before rehydration of the tissues occurs, and presenting subsequent blindness (or desensitization) and thereby presenting a challenge to the ability of the treated insect to survive.

Additionally, antenna function and leg motility are related to the cuticle. Normally, the cuticle is sclerotized, making it drier, stiffer, and resistant to degradation via cross-linking in the protein-chitin.[x] In the joints, however, the cuticle is unsclerotized to allow for flexibility. This "weakness" means that IR exposure could change the ability of the internal chitin to retain water in tissues necessary for mobility (appendage muscle, connective tissue, condyles (joint tissue)); such changes can cause damage to insect joints, thereby disabling the insect. The present invention is useful in the control of insects in general, an example of which is the glassy winged sharp shooter egg mass as a target in a host of living plant tissue.

General Biology—Microorganisms

Microorganisms have existed on the earth for over 3.5 billion years. In this time, they have proven to be very adaptable, pervasive, and versatile. In fact, the early bacteria of two billion years ago established the major metabolic pathways which are characteristic of life forms today. Continued reproductive and adaptive success have ensured that the physiology and biochemistry of bacteria and fungi are a reflection of billions of years of genetic responses to a changing environment.[xi,xii]

The classification of microorganisms is based upon the 1969 R. H. Whittaker system proposal that suggests that there are five kingdoms based upon three principal modes of nutrition. The kingdoms are the Monera (bacteria), Protista (principally algae and protozoa), Plantae (plants), Fungi (yeast and molds), and Animalia (nematodes-roundworms, platyhelminthes-tapeworms/flukes, and other phyla). The first two kingdoms are the foundation, out of which the remaining three have evolved. The nutritional modes upon which this system is based are Plantae (photosynthesis), Fungi (nutrient uptake by adsorption), and Animalia (nutrient uptake by ingestion). Additionally, non-cellular infectious agents, such as viruses (animal hosts), viroids (plant hosts), prions (infectious proteins), and virino (nucleic acid enclosed in host protein) constitute a microbial population which should also be included in the taxonomy.[xiii]

Fungal Physiology—Chitin

Fungal chitin is chemically identical to that of arthropods and is confined exclusively to the cell wall in all but one class where it can also be found as cytoplasmic inclusion granules.[xiv] In fungi, the role of chitin is to maintain cell wall shape and rigidity. The cell walls of fungi are composed principally of polysaccharides (sugars) and small amounts of lipids, proteins, and other inorganic ions. The polysaccharides are found in two major structures: threadlike microfibrils, and a less organized matrix. The structure of the microfibrils, the principle structural component of the cell wall, is that of separate polysaccharide chains wound about the others forming coarse, strong threads. These threads are embedded in the matrix, an aggregation of smaller polysaccharides that appears unstructured and granular. The matrix is also composed of proteins and lipids; these make up generally less than 10% and 8% of the matrix by weight, respectively. The fungal wall is analogous to reinforced concrete with the microfibrils acting as the steel rods and the matrix as the concrete.[xv]

The microfibrils themselves are composed of chitin, cellulose, or other noncellulose-based glucan. Structurally, chitin is an unbranched polymer of β-1,4-linked N-acetyl D-glucosamine units. The presence of chitin in the fungal cell walls of several of the major fungal groups is a distinguishing feature that sets fungi apart from higher plants. One basis of classification of fungi is the occurrence of matrix sugars and microfibrils since the carbohydrate distribution in the matrix differs from one taxonomic category of fungal groups to another.[xvi,xvii]

There are chemical differences between the amount of chitin present (dry weight) in the fungal cell wall and the particular life cycle structures. The amount of chitin found in the sporangiophores (the spore forming fruiting body) in one species, *Mucor rouxii*, is 18% by dry weight. The cell wall of other fungi can contain as much as 39% to 58% chitin, also by dry weight.[xviii] Phospholipids and sphingolipids are the major lipids found in fungal membranes; these lipids are polar molecules, which contain a hydrophilic 'head' and a long hydrophobic 'tail.' The plasma membrane, which is the regulator of material passage from inside and outside of the cell, is composed of equal parts lipids and proteins, small amounts of carbohydrates, and sometimes nucleic acids are found.

Figure 6:
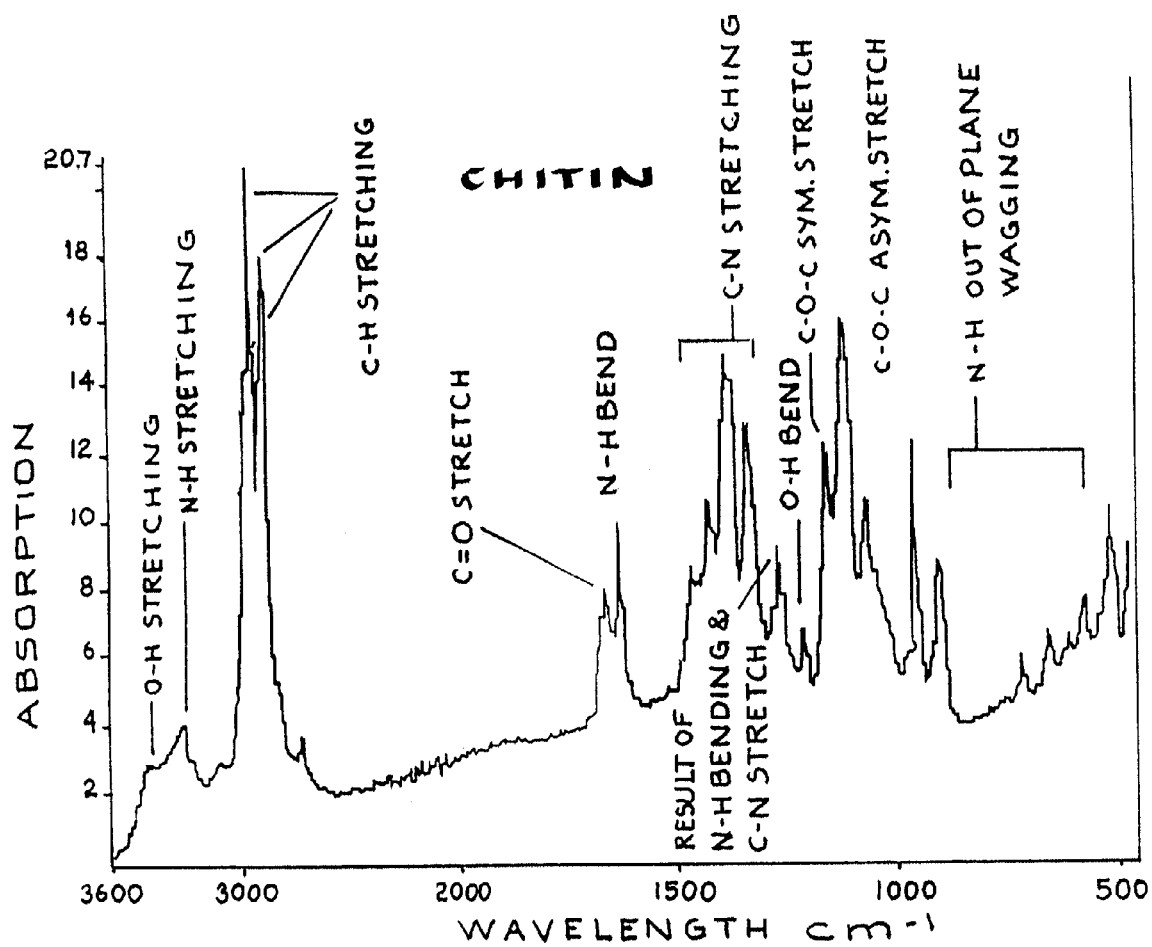
FIG. 6 Raman spectra of chitin.

It is important to note that in an *Aspergilus* sp. the amount of chitin increases within the cell wall just prior to germ tube emergence. Alterations in the concentration of cellular components, such as chitin, have been utilized as a way to determine fungal growth especially in assessing the growth of fungal plant pathogens.[xix] According to Griffin, controlling pathogenic fungi "through inhibition of chitin synthesis would seem to be an ideal mechanism for selective fungicides without deleterious side effects on the host. However, very few fungicides have been discovered with this kind of activity".[xx] However, since chitin is IR active, the process of disrupting the chitin (and therefore the cell walls) of fungi by differential processing with narrow bandwidths of light can be a practical alternative to chemical fungicides. See FIG. 6 for the Raman spectra of chitin.

Molecular Vibrational Transitions and Infrared Spectroscopy

All matter consists of atoms and molecules. In a molecule, atoms are held together by the three-dimensional arrangement of their electrons. In some substances, the arrangement of the charged components of the atoms (the positively-charged nuclei and the negatively-charged electrons which surround them) is symmetric, and no net accumulation of charge (a dipole moment) exists in any area of the substance. Such non-polar substances are unable to interact with an oscillating electric field (light) and, therefore, completely transmit microwave and infrared radiation. Molecular oxygen and nitrogen ($O_2$ and $N_2$), two major components of air, are examples of non-polar molecules; both are homonuclear diatomic molecules which, by virtue of their symmetry, have no net dipole moment or charge. Interaction with an oscillating electric field, and, therefore, the absorption of microwave and infrared radiation, can only occur when a substance has an uneven charge distribution (a dipole moment). These polar molecules, such as carbon dioxide ($CO_2$) and water ($H_2O$), act like tiny magnets in the presence of an applied electric field and try to align themselves such that their dipole moments line up with and do not oppose the charge of the electric field. Since polar molecules are capable of this interaction with oscillating electric fields (light), these molecules have the potential to absorb infrared and microwave radiation.

As mentioned, polar molecules have the potential to absorb light energy of any wavelength in the electromagnetic (EM) spectrum. The range of wavelengths of light included in the EM spectrum is so vast that it has been divided arbitrarily into separate regions of light. These regions are listed below:

| Region: | Wavelength Range: | Transition/Effect: |
| --- | --- | --- |
| power | one light second → 3 km | Nuclear Magnetic Resonance |
| radio | 3 km → 30 cm | Hyperfine Electronic Structure |
| microwave | 30 cm → 1 mm | Molecular Inversion & Rotation |
| far infrared | 1 mm → 3 μm | Vibrational & Rotation |

-continued

| Region: | Wavelength Range: | Transition/Effect: |
| --- | --- | --- |
| near infrared | 3 μm → 700 nm | Vibrational |
| visible | 700 nm → 400 nm | Electronic & Vibrational |
| ultraviolet | 400 nm → 200 nm | Electronic & Vibrational |
| vacuum UV | 200 nm → 3 nm | Atomic Transitions |
| X-rays and γ-rays | <3 nm | Atomic Transitions Nuclear Transitions |

When a molecule absorbs a photon (a packet of light energy), the energy of the molecule is increased by the energy of the photon. The energy of a photon ($E_{photon}$) is inversely proportional to its wavelength ($\lambda$) (shorter wavelengths signify greater energy) by the following relationship: $E_{photon}=hc/\lambda$ (h and c are constants). Photons can also be described by the frequency ($\nu$) of their light, which is related to wavelength by the following: $\nu=c/\lambda$. Using frequency, the change in energy ($\Delta E$) experienced by a molecule with the absorption of a proton is equal to $h\nu$. This additional energy manifests itself in changes in the electronic, vibrational, and rotational states of the molecules known as quantum transitions. For the process of the present invention, generally, EM energy with wavelengths shorter than one light second and energies less than ten electron volts are of primary interest. Absorption of microwave radiation causes transitions between molecular rotational states, while infrared radiation causes transitions between vibrational states. Absorption of infrared radiation will be discussed in greater detail.

While molecules can absorb IR radiation, they can not absorb it continuously across the entire range of possible wavelengths. Nature has dictated that only certain energies are allowed for each polar site; thus only certain energies (the "quantum" of quantum mechanics), specific to the chemical bonds and atoms involved, can be absorbed. If one considers a chemical bond to behave like a spring between two weights (atoms), it can be treated by classical physics as a harmonic oscillator. Like a spring, the bond will experience a restoring force if it is "stretched" beyond its equilibrium position; this force results in the atoms moving about their equilibrium position with harmonic motion (the motion of a pendulum). The potential energy (V, the ability of the system to do work) of the bond in its stretched position is a parabolic function of the displacement distance (x) and is given by the following: $V=\frac{1}{2}kx^2$. The constant k is the bond force constant and is a characteristic feature of the bond. Given in units of $N/m^2$ (Newtons per meter squared), k is directly proportional to the "strength" of the bond and its tension as a harmonic oscillator. Because molecular vibrational motion is quantized, the Schrodinger equation for a harmonic oscillator can be used:

$$\frac{-\hbar^2}{2\mu}\frac{d^2\psi}{dx^2}+\frac{1}{2}kx^2\psi=E\psi$$

Solving this equation for its permitted energy levels, and thus the allowed vibrational transitions of the molecule, gives:

$$E_v = \left(v + \frac{1}{2}\right)\hbar\omega$$

where v is the vibrational quantum number and equals 0, 1, 2, 3 . . . and where $$\omega = \sqrt{\frac{k}{\mu}}.$$

The variable μ is the reduced mass of the two atom system described here and is equal to the following:

$$\mu = \left[\frac{1}{m_1} + \frac{1}{m_2}\right]^{-1}$$

where $m_1$ and $m_2$ are the masses of the atoms of interest. The use of the reduced mass of the system can be easily understood if one imagines that one of the atoms is much heavier than the other; the smaller atom will experience a much larger displacement than the bulkier atom and will, therefore, have a greater influence in the vibrational frequency of the system.

While the exact energy levels are of little experimental use, the energy differences between vibrational levels are of extreme importance; these energy differences are equal to the energy of the photons that will be absorbed by the molecule, which in this case is a simple heteronuclear diatomic molecule like HCl (hydrochloric acid). In order to calculate the differences between these levels, consecutive quantum numbers are plugged into the energy expression and subtracted from each other:

$$\Delta E = E_{v+1} - E_v = \hbar\omega$$

Since this expression has been derived using general quantum numbers, it can be seen that the energy difference between all vibrational levels are equivalent, giving a uniform ladder spacing to the vibrational structure of the molecule. It is interesting to note that the energy of the ground state vibrational level (v=0) is not zero:

$$E_0 = \frac{1}{2}\hbar\omega$$

This is significant because it means that the vibrational motion of the bond never ceases; instead, even in its lowest energy state, the atoms oscillate continuously about an equilibrium position.

However, while molecules are capable of making transitions between various vibrational levels, not all transitions are allowed. Selection rules, governed by the laws of quantum mechanics, determine which transitions are allowed. The most general selection rule for any molecular interaction with the EM field was given above: in order to absorb a photon in the infrared range, a molecule must possess at least a transitory dipole moment (redistribution of charge) which oscillates at the same frequency as the photon. (In order to absorb microwave radiation to effect a rotational transition, a molecule must have a permanent dipole moment at the desired frequency.)

For vibrational transitions, a more specific selection rule applies: the quantum number v of the vibrational state can only change by one ($\Delta v = \pm 1$). Thus, since most molecules are in their ground vibrational states at room temperature, the most dominant transition in a vibrational spectrum would be the single line representing the v (0→1) absorption. This simple spectrum is not seen however, for even the elementary molecules; several complications serve to convolute vibrational spectra. First, for those molecules with a permanent dipole, the absorptions due to microwave transitions are embedded in the vibrational spectra. However, for complex polyatomic molecules the rotational transitions are obscured by the vibrational absorptions and tend to merely broaden the absorption peaks. The largest contribution to the complex appearance of vibrational spectra is due to anharmonicity in motion of the bonds. The quantum mechanical expressions and selection rules for vibrational transitions were all derived under the assumption that molecular bonds behave like harmonic oscillators. This assumption, however, only approximates bond behavior near the minimum potential energy state. When bonds are vibrationally excited to higher and higher levels, their motion becomes anharmonic because the restoring force of the vibration is no longer proportional to the displacement force. In the vibrational transition ladder, the subsequent energy levels are no longer evenly spaced, but converge, becoming less widely spaced until a maximum energy level is reached. At this energy maximum, the bond dissociates, a property not predicted by the harmonic oscillator equations. Anharmonicity affects the spectral appearance in two ways: 1) vibrational transitions tend to occur over a small range of frequencies, resulting in broader peaks instead of sharp absorption bands, and 2) the $\Delta v = \pm 1$ selection rule is not strictly followed. Weak absorptions (known as overtones) are also seen, corresponding to "forbidden" transitions, such as v (0→2, 0→3, etc.).

While anharmonicity complicates the picture of excited vibrational motion occurring between atoms which behave like weights on a spring, this idea is a valuable conceptual tool which allows understanding of the motion which is excited in molecules when an IR photon is absorbed. In a linear diatomic molecule, the only motion which may be excited is a stretch in the bond. In polyatomic molecules, however, the symmetrical and asymmetrical stretching of bonds may be IR active, as well as bending and wagging motions as the angles between bonds are changed. Such motions are known as normal modes, independent motions of atoms or groups of atoms that can be excited without causing any other movement. The number of normal vibrational modes in a molecule can be calculated with the following formulas:

(nonlinear): $3N-6$

(linear): $3N-5$

Where linear or nonlinear refers to the geometry of the molecule and N is the number of atoms in the molecule. Therefore, in a non-linear molecule with twelve atoms, there are thirty normal vibrational modes which will absorb IR radiation if they are allowed by the selection rules. Vibrational spectra, generated by measuring the radiation absorbed by a molecule at different frequencies, are extremely complex for all but the simplest of molecules.

However, while the spectra of individual molecules are difficult to interpret, different groups in the molecules give rise to absorptions at characteristic frequencies and intensities. Functional groups, defined as an atom or atoms in a larger molecule with characteristic chemical behavior, absorb IR radiation at frequencies and intensities that remain approximately constant between molecules. For example, molecules with a carbonyl group (a carbon atom double-bonded to an oxygen atom) show IR absorptions between 1650 $cm^{-1}$ and 1800 $cm^{-1}$, depending upon the exact chemical environment of the group. Since every absorption peak can theoretically be assigned to a molecular motion or functional group motion, the identity of unknown compounds can be elucidated from their IR spectra.

Standard Mode Spectroscopy

EM spectra are obtained with a spectrophotometer designed with a radiation source, a monochromator and a detector for each range of wavelengths. Spectra were obtained in the range from 200 nm through 800 nm with the UV visible Hewlett Packard (HP) spectrophotometer. Spectra from 800 nm through 2,500 nm were gathered using several types of near IR spectrophotometer. Spectra were obtained from 2,500 nm (2.5μ) through 25μ using a Mattson 3020 infrared spectrophotometer and attachments. Spectra in the range 25μ through 1 mm are obtained with Far IR spectrophotometers. Spectra in the range from 1 mm through the 10 kilometers are obtained with radio frequency (RF) spectrophotometers. Also, spectra were gathered from many spectral libraries from many different sources or derived from molecular modeling programs.

Experimentally, IR spectra are easily obtained with an IR absorption spectrometer. Most absorption spectrometers have the same basic components: a source of radiation, a sample holder, a monochromator (allows the selection of a single wavelength) and a detector. The components vary depending upon the properties of the sample, the portion of the EM spectrum used, and the degree of precision and accuracy desired by the researchers. In the studies described herein, using the general process known to those skilled in the art, three types of Mid IR spectra were obtained for each sample: absorbance, transmission, and diffuse reflectance spectra. All absorbance and transmission IR spectra were obtained from a Mattson 3020 infrared spectrophotometer. The diffuse reflectance absorbance spectra were obtained from a Grasby S Specac 4500 Series Diffuse Reflectance Infrared Fourier Transform (DRIFT) kit. The wavelength range for all data was between 400-4000 $cm^{-1}$ (wavenumbers) or 2.5 to 25.0 μm (microns); each spectrum was taken at 60 scans at 4 $cm^{-1}$ intervals.

In absorbency and transmission IR studies, a sample is exposed to light of varying wavelengths and the intensity of the light, which passes through the sample, is compared to the known intensity of the original beam. Transmission IR gives results according to the amount of light which passes through the sample (is transmitted), while absorption IR gives results according to the light absorbed by the sample. The two sets of data are mathematically related by the following:

$$A = -\log T = -\log \frac{I}{I_0}$$

Where A is the absorbance, T is the transmittance, I is the intensity of the light which passes through the sample, and $I_0$ is the intensity of the original beam. The absorbance (A) of a sample is also dependent upon the sample thickness and path length according to Beer's Law:

$$A = \epsilon c l$$

where c is the sample concentration, l is the sample path length and $\epsilon$ is the extinction coefficient.

The Mattson was background checked as often as possible between sample sets (10 minutes default). Sodium chloride (NaCl) sample cells were utilized for natural oils, plastic films, and non-hydrated (non-water containing) samples. Silver chloride (AgCl) sample cells were utilized for hydrated samples.

The DRIFT unit background was either a clean sample pad or oven-dried potassium bromide (KBr). The diffuse reflectance was used to examine the surface of both animal and plant samples upon a dime sized sample pad. The sample tissue was rotated 90 degrees and rotated again 90 degrees to observe any changes in absorbance. Oven-dried samples (30 minutes to 1 hour at 110° C.) were mortared and pestled with oven-dried KBr in a 20:1 (KBr:sample) ratio. Oven-dried KBr was used as the background.

Ultraviolet/Visible Spectrophotometer:

Samples were scanned from 190 nm to 1100 nm utilizing a Hewlett Packard 8453 diode array spectrophotometer and 845 x UV-VIS spectrum station. Sample cuvettes were quartz or plastic. The background was taken utilizing distilled water. Some samples were immersed in distilled water to minimize light scattering or to facilitate proper dilution and/or suspension. Other samples were crushed then centrifuged to separate liquids from solids; each component was then tested separately.

High Power Spectroscopy, Active Spectroscopy and Destructive Spectroscopy

High Power Spectroscopy

High power spectroscopy is used for partially opaque, dense and thick samples out of the range of standard spectrophotometers. Standard photometers utilize a source such as a nernst glower or globar with total a emission in the 20 watt or less range total for all wavelengths emitted (mid IR range consist of 3400 separate frequencies) giving a per line power of 0.005 watts (5 mw) or less. This light energy covers an area of about 6.5 $mm^2$ giving a flux density less than 0.7 $mw/mm^2$. High power spectroscopy uses emission sources with powers up to 10 $watts/cm^2$.

Active Spectroscopy

Active spectroscopy spans the power range between high power spectroscopy and destructive spectroscopy. Active spectroscopy utilizes power levels capable of actively changing physical properties of sample. Adding a Gas Chromatograph (GC) mass spectrometer allows investigators to track changes by sampling test-cell atmospheric gasses discharged from the samples during testing. Active spectroscopy is the test platform for the evaluation of treatment and therapeutic action. In-vivo therapeutic devices will be derived directly from this form of spectroscopy.

Destructive Spectroscopy

Destructive spectroscopy (in vitro only) extends the spectroscopic investigation to the point of destroying target and is used to explore the damage threshold of the host. Processing the sample to the point that it starts to degrade establishes hard stops for in vivo trials. Samples can be processed beyond the damage thresholds to investigate how both target and host materials react to very high energy at a specific wavelength. Monitoring samples during processing by coupling a GC mass spectrometer to the sample chamber;

as the sample degrades it will offer further insight to chemical breakdown and reactions.

The three types of high-energy spectroscopy described have some common components, a source, a sample holder and a detector. Monochrometer are used only when polychromatic sources are utilized, laser or line sources emitters do not require their use.

Detectors

Detectors are transducers and its purpose is to intercept or receive a signal or beam of electromagnetic radiation and convert it into the form of an electrical or digital signal. The responsiveness of a detector depends on such factors as type, the wavelength of the radiation and the temperature of the detector. Detectors include Golay cell, radiation thermocouples, thermopiles, galvanometers, bolometers and photo-detectors (photodiode, CCD, CMOS).

For operations at a low frequency (of the order of 5 Hz) the Golay cell is about the best un-cooled thermal detector available at present. Thermocouples offer good utility when properly matched to amplifier by means of a coupling transformer. When a detector for high-energy situations is required, one must use a cooled detector such as cooled bolometer. Cooling generally improves the frequency response and reduces noise as well.

The essential difference between Quantum type or photo-detectors and thermal detectors is thermal detectors absorb quantum of frequency ν produces an effect proportional to ν (energy per quantum=hν) whereas in the photo-detectors a quantum either produces an effect largely independent of its frequency or produces no effect at all. Many applications require photo detectors with the ability to quantitatively respond to low incident-light levels achievable with avalanche photodiode (APD).

Charged-coupled-device (CCD) arrays are built up out of pixels consisting of metal oxide-silicon (MOS) capacitors. Each of these is an insulating silicon-dioxide layer over a p-type silicon substrate that is capped by a thin metal electrode. With an applied bias, hole move away from a depletion layer in the silicon beneath the gate, creating a potential energy well. Electron-hole pairs are generated when the device is illuminated and the electrons accumulate in this well, with the accumulated charge proportional to the irradiation. Charge readout involves sequential transfer of the charge from pixel to pixel until it is detected at the edge of the CCD chip. CCD has a dynamic range of 1.1 µm through the ultra violet frequencies. These devices also have lower dark noise levels than CMOS imagers, and so have greater sensitivity and greater dynamic range—the ratio between the darkest and brightest lights that can be recorded. Complementary-metal-oxide-silicon (CMOS) is extremely cheap to produce compared to CCD. CMOS imagers expose a line at a time and then transfer that line into an output register which offers information in an additional format. High power sources like lasers may in some cases overwhelm the detector. In this case, the appropriate type of detector is implemented per application. Antenna and signal processor are utilized in the microwave, radio wave and longer wavelengths.

Sample Holders/Test Cells

Test cells and sample holders can have many different configurations but requires certain components. Primarily they must have windows that will transmit EME at appropriate frequencies. Windows are fabricated from many different substances and must fit all requirements of sample, wavelength and environmental conditions etc. Alkali halides (salts) NaCl, KCL, KBr, CsBR, CsI is chemically incompatible with water. Metal fluorides $MgF_2$, $CaF_2$, $SrF_2$, $BaF_2$, are incompatible with ammonium and acids and are sensitive to thermal or mechanical shock. Chalcogenides ZnS, ZnSe, CdS, CdSe, CdTe have some toxic properties with dust and when oxidized. Glasses $SiO_2$, $As_2S_3$, AMTIR, HMFG, are inexpensive but limited to the visible and NIR range. Plastics HDPE, TPX, TFE, FEP are inexpensive but are susceptible to cold flow and deform with heat. Sample chambers are constructed of stainless steel or other low reactive materials. Also, the chamber is most often fitted with ports to allow gasses to be removed for analyses. The cell is mounted on a trunnion mount for quick alignment after sample change. The size of the cell or chamber is designed to accommodate large and thick samples. Test cells for the wavelengths longer than about 1 mm are fabricated from non-metallic materials such as quarts ($SiO_2$) or other non-absorber at the test frequencies. The test cells are often tubular and are placed in the center of the transmitting coil, many are double walled.

Flux Optimization

Flux optimization applies to both analysis and treatment, EME emitted from the source (flux) is optimized prior to exposure to sample cell or for treatment; this can be accomplished in numerous manners including, but not limited to, filtering, focusing, beam expanding, collimating, reflecting, grating, are considered passive optimization. Pumping, shifting, doubling, Q switching, pulsing, accelerating, exciting are electromechanical or electro-optical means of changing the form of a beam or delivery rate through adding energy to a system or converting it to a desired wavelength. Focusing optics, beam expanders, and collimators work at lower powers in the visible and NIR, but often overheat and break down under higher power of laser and other sources. An optical system that does not require transmission is preferred. Mirrors are used to manipulate and optimize beam or energy or used in high power spectroscopy and will need to be first surface.

Laser output power must be controlled with great precision, controlling output can be accomplished electronically or implementing a scanning or rotating mirror offers good utility. Flux density is Power over Area times Time thus scanning at fast rate over a large area will translate to low flux density, compared to scanning the same area at a slow rate which would translate to a high flux density. Flux density can be expressed in watts per second or in joules, (one watt second is equal one joule). A laser with 100 watt output and a 3 mm beam diameter would produce 33.33 watts/mm/second; this same beam scanned over 1 $cm^2$ will deliver 1 watt/second/$cm^2$.

Standard configuration for high power, active and destructive spectroscopy would typically have a tunable or single wavelength laser as a source that would be focused on a galvanometer based scanning mirror. The energy reflected from scanning mirror is directed through the test cell and received on the opposite side of sample as thermal image, transmitted energy or optical image with matched detector.

Emitters

Infrared emitters range from very sophisticated stimulated emission sources, i.e. gas discharge tubes, lasers, masers, klystrons, and free electron lasers (FEL), to black and gray body emitters, which emit based on temperature. Many stimulated emission devices are undesirable due to low power or inefficiency in power conversion or are just too large for some applications. The emission source must have efficiency matched to the process to be performed. Stimulated emission devices may not be suited to agriculture applications where large bulk products of lesser value may not warrant the cost of the treatment process. Stimulated emission sources are many times best suited to medical applications or for use on products with high value or where low power will offer the desired effect. Black and gray body emitters are very useful in the visible and near IR but do not have sufficient energy with wavelength longer than about 6μ. Lasers have been developed with a wide range of wavelengths. Some are very tunable such as the FELs. It is preferable to use more efficient emitters in the process of the present invention.

The carbon dioxide ($CO_2$) laser has good utility as a source for the light energy needed to cause photobiological disorders in insects and/or microbes. Using gaseous carbon dioxide as the lasing medium, these lasers produce a band of radiation from 9 to 11 microns (μm). Gaseous nitrogen ($N_2$) is mixed with $CO_2$ and is vibrationally excited by electric discharge. Because the energy level of the excited nitrogen molecules matches that of the asymmetric stretch of the $CO_2$ molecule, energy is transferred to the now excited carbon dioxide via intermolecular collisions. Lasing is then seen in the transition from the lowest level of the asymmetric stretch excited state to the lowest excited level of the symmetric stretch. This level remains unpopulated by collisions and does not acquire a significant population from the lasing process because $CO_2$ molecules in this level quickly dissipate energy thermally in order to return to their stable ground state. The resulting radiation band can be separated into roughly one hundred discrete lines; any of these discrete, narrow bandwidth lines of radiation can be selected, thereby tuning the laser to produce monochromatic infrared radiation. $CO_2$ lasers are also attractive as radiation sources because the intensity of the light they produce is several orders of magnitude greater than other infrared sources. The 10-micron wavelength, close to the most intense radiation produced by the laser, is especially useful in the treatment of head lice, as illustrated in Example 5. Research we have conducted has shown that human hair and skin have low absorption of infrared radiation at this wavelength; therefore, while the radiation disrupts the insects to such an extent that they cannot survive, the hair and skin of those who received the treatment remains unaffected.

The Theory of Lasers

Since their initial development, lasers have been implemented into nearly every facet of modern life. From grocery store scanners to compact disc players, lasers represent a versatile area of applied optics and one of the possible sources of emission for the process of the present invention. The term laser is actually an acronym for the following: Light Amplification by Stimulated Emission of Radiation. The emission process encountered in lasing differs from those seen in fluorescence and phosphorescence; in these two quantum processes, molecules are raised to an excited state by the absorption of an incident photon of wavelength $\lambda_1$. After some of the photon's energy is lost through thermal processes, the molecule will emit another photon of wavelength $\lambda_2$ in order to return to its lower energy ground state. Because some energy is dissipated, the emitted photon has a longer wavelength (lower energy) than the absorbed photon ($\lambda_1 < \lambda_2$).

In lasing, however, the excited state of a molecule is stimulated to emit a photon of wavelength $\lambda_n$ by the presence of radiation of the same frequency. The lasing process is also capable of a growth in intensity not seen in the other two processes; a greater population of radiation of wavelength $\lambda_n$ (determined by the quantum transitions made by the chosen molecule) will result in the emission of a greater number of corresponding photons from the excited molecules. However, the probability of emission is equal to that of absorption, which under normal circumstances where equal numbers of molecules are absorbing and emitting photons, would make this growth in intensity impossible. In order to see the lasing effect, the Boltzmann distribution of molecules must be overcome. This distribution finds that most molecules will be in their ground states (lowest energy states) before sample excitation. Sample excitation with an equal probability of absorption and emission will not result in a net emission of light of wavelength $\lambda_n$. However, the Boltzmann distribution could be reversed if the population of excited molecules was greater than that of ground state molecules, in which case the introduction of radiation ($\lambda_n$) would result in a net photon emission from the sample. This population inversion would require the creation of an energetically unfavorable metastable excited state with a lifetime long enough to undergo stimulated emission (longer that the fluorescence lifetime).

Such a population inversion was first created in a three-level laser. In this procedure, a molecule is excited to a high-energy state, X*, through a rapid transition done with intense light known as pumping. The molecule then undergoes rapid thermal energy loss to a less energetic state, X. The laser transition, stimulated by incident $\lambda_n$ photons, is then the slower transition of the molecule from the metastable state X to its ground state, S. While a population inversion is created in this system, it is inefficient; a great deal of energy must be expended in exciting molecule from S→X*.

As a result of selecting a four-level laser, a more efficient population inversion is possible. In this system, a molecule is pumped in a fast process to X*. It then undergoes thermal energy loss or intersystem crossing to a lower metastable excited state, W*. Lasing is then seen as the molecule emits a photon in a slow process to a third excited state, W. Finally, the molecule returns to its ground state, G, through a fast process. Since W and W* are both initially unpopulated, the presence of any molecules in W* creates a population inversion. Also, since the transition from W→G is rapid, there is no build-up of population in W to overcome the inversion, and a maximum of efficiency is attained.

However, the wavelengths of incident radiation, which will result in lasing are not unlimited. They are initially restricted to the laser cavity, the tube which holds the laser medium. Laser cavities are mirrored on both ends so that light can be reflected back and forth through the medium. Much like sound waves in a closed tube, the lasing wavelengths depend upon the length of the cavity:

$$N(0.5\lambda) = L$$

where L=cavity length, N=1,2,3 . . . , and the refractive index of the medium is 1.

The lasing wavelengths are more generally limited by the inherent quantum transitions of the chosen laser medium. In the previous four-level example, the incident radiation needed to instigate lasing would be chosen to exactly match the wavelength ($\lambda_n$) of the photon emitted in the transition of W*→W. (Normally, the length of the cavity would then be chosen such that $2L/N = \lambda_n$). Such resonant photons would stimulate laser activity; one incident photon would result in the emission of a cascade of photons from the laser medium, radiation, which could be extracted from the cavity if one of its mirrors were partially transmitting. Because of these wavelength restrictions, laser light has very low divergence, is highly monochromatic and coherent. Laser output has a high intensity and narrow bandwidths, properties which augment the value of lasers in both scientific and industrial applications.

The Process

Generally, matter is selectively exposed to a specific wavelength or wavelengths of electromagnetic energy in sufficient flux density per wavelength to cause or promote a desired effect. The process includes, but is not limited to, disinfecting, denaturing, disinfesting, disrupting, dehydration, marking, illuminating, or tagging of one or more of the substances present. The process takes advantage of the spectral differences within the substance or within a mixture of substances. Energies are applied to cause wavelength-dependent reactions resulting from differential absorption. The process can be used for a wide variety of applications, a few of which are illustrated in the examples below.

A host or product considered for treatment and the associated target or infestation are subjected to testing to determine their spectral properties. These spectral properties and known processing parameters and constants are used to solve the following equation.

$$P/A \times t \times (A_\lambda) = E_a = m_1 \times C \times (T_c - T_\alpha)$$

Where P=Power, A=Area, t=time, $A_{,\lambda}$=Absorption factor, $E_a$=Energy absorbed, $m_1$=mass of substance, C=Heat capacity, $T_c$=Temperature Critical, $T_\alpha$=ambient temperature.

Absorption Factor=Absorption derived from spectra wavelength dependent.

Temperature Critical=Desired Effect.

Compiled spectra from host and target or infestation are compared; frequencies that exhibit the highest or sufficient differential absorption are considered for use in processing. Frequencies considered are then evaluated for availability, power conversion efficiency, available flux density, band width of emission, efficiency after filtering or frequency modulation, and transparency or reflectivity of host at the considered wavelength.

Frequencies considered are then evaluated for (1) Availability of an emission source at the desired wavelength. Not all wavelengths are available currently (2) Power conversion efficiency: Treatment must be cost effective per application—the more efficient, the better; if efficiency is not high enough, the process can take too long and potentially cause a greater undesirable effect in the host.

(3) Available flux density: Flux density=power/area×time

Ex: 1000 w per millimeter$^2$–high power

Ex: 1000 w per meter$^2$–low power

Available flux density considers the potential source having sufficient power at the desired wavelength to bring target substance to temperature critical. A dense enough emission over the appropriate area to achieve desired result is required.

Flux density must have sufficient energy to satisfy the equation $$P/A \times t \times (A_\lambda) = E_a = m_1 \times CX(T_c - T_\alpha)$$

to reach temperature critical before energy has time to dissipate.

(1) Bandwidth of emission: Will the emission source considered need to be filtered? Generally, a narrow bandwidth is desired, but may depend on the spectral properties of the host and the target or infestation. It is of particular importance to avoid undesired effects on host if host has absorption peak close to the peak in the target or infestation that is being evaluated.

(2) Efficiency after filtering or frequency modulation.

Unwanted frequencies can be filter from a source with broader emission i.e. Black body emitters. Frequencies emitted from lasers can be controlled, by frequency shifting, modulation through spin flip Raman scattering or frequency doubling with non-liner crystal or other means. Frequency modulation or doubling is at best only 10% efficiency. Determine transparency and/or reflectivity of host at considered wavelength. If the infestation is located on the surface, the host need only be a non-absorber or a reflector at treatment wavelength using a single wavelength or single band of wavelengths. This non-transmittance or reflectance capability results in more frequencies available for treatment. If the infestation is embedded in the host the host must have some degree of transparency at treatment wavelength to allow the energy to reach the infestation or have the capacity to conduct or transmit said energy to infestation location. Host and related infestation with a low degree of differential are preferably targeted at several differential sites with appropriate wavelengths. This multi-mode processing, or multiple wavelength treatment can utilize any or all wavelengths that do not cause an undesirable effect to host.

It is important for the host to be a non-absorber at selected frequency. In other words the host preferably does not absorb, or absorbs very little, at the selected frequency. This is referred to as the selection of a "clear path" or a frequency at which the target or infestation will be affected as desired without harm to the host. In order to select a clear path, it is not always desirable to select the frequency with the greatest difference in absorption between the host and target if the host also absorbs at that frequency. More importantly to select a frequency at which the host is least effected. Finally, the physical state of the product, and the method of conveying the product to exposure site must be evaluated.

When a wavelength has been selected, flux density tests are conducted. For suitable hosts, samples of the host or product are subjected to increasing intensities of the selected wavelength to the point when the host is determined to have suffered an undesirable effect. Suitable hosts are those for which it is possible to take a sample for experimentation and for which it would not be undesirable to effect a change in a sample from the host. Examples of suitable hosts include grains, raw meat or fish, and paint. Clearly any human or animal that can be treated by the processes of the present invention would not be tested in this way. In the case of a human or mammalian host, tissue would be tested from samples that have been removed from the host. Alternatively, the clear path can be initially calculated mathematically based on known spectral absorption using the equation $$P/A \times t \times (A_\lambda) = E_a = m_1 \times C \times (T_c - T_\alpha)$$

The infestation is also treated in the same manner and monitored for kill or for disruption of one or more metabolic functions. The difference in absorption is realized and parameters for processing are established. Process time is limited by several factors; the first being the magnitude of differential absorption. If the host and related infestations have a high degree of differential (a minimum of twenty times differential is preferred) process times are minimal provided high intensity sources are available with narrow band emission at the desired wavelength. Host and related infestations with a low degree of differential are preferentially targeted at several differential sites with proper wavelengths. The physical state of the product and the type of apparatus and system used for conveying the product to the exposure site is also evaluated.

The process is generally carried out according to the following steps:

1. Classify Host (Product).
   Identify UV/visible absorption spectra
   Identify Near IR (NIR) and Mid IR diffuse reflectance spectra
   Determine NIR and Mid IR transmittance spectra
   Determine NIR and Mid IR absorption spectra
   Determine Far IR absorption spectra
   Determine Far IR transmittance spectra
   Determine RF absorption spectra
   Determine RF transmittance spectra
   Combine the spectral properties and record spectral fingerprint for the host. Any one or more of the spectra listed can be used alone or in combination in order to classify the host.

2. Classify Target or Infestation (e.g., Pest, Insect, Microbe, Mold, Fungus, Enzyme, Protein etc.).

Identify UV/visible absorption spectra

Identify NIR and Mid IR diffuse reflectance spectra

Determine NIR and Mid IR transmittance spectra

Determine NIR and Mid IR absorption spectra

Determine Far IR absorption spectra

Determine Far IR transmittance spectra

Determine RF absorption spectra

Determine RF transmittance spectra

Combine the spectral properties and record spectral fingerprint for the target or infestation. Any one or more of the spectra listed can be used alone or in combination in order to classify the target.

3. Compare the Spectral Fingerprints of the Target or Infestation with That of the Host.

Identify areas of differential absorption between target or infestation and host.

Identify all possible peaks for selection for the target or infestation.

Calculate the magnitude of difference between the peaks of the host and the peaks of the pest (the differential absorption).

Evaluate frequencies that exhibit sufficient differential absorption. Twenty times differential is a preferred minimum for single site treatment. The preferred differential can also be satisfied through multiple site treatment that cumulatively offers this differential.

Evaluate frequency for availability, power conversion efficiency, available flux density, bandwidth of emission, efficiency after filtering or frequency modulation, and transparency of the host at the considered wavelength.

4. Select a Known Source.

Tune or modulate to proper frequency if required.

Perform Flux Density Experiment.

Expose the host to higher and higher intensities of EM energy until the point when host is determined to have suffered undesirable effects. (This is only for a suitable host; for other hosts, a mathematical determination is used.) This determines the maximum limits of exposure.

Expose the target or infestation to higher and higher intensities of EM energy until disruption of one or more metabolic functions is observed or the infestation is destroyed. (This is only for a suitable host; for other hosts, a mathematical determination is used.) This will set the minimum limit for exposure.

For example:

Infestation at 6 Joule/$cm^2$ for pest kill.

Host at 42 Joule/$cm^2$ has received damage

Host can tolerate 40 Joule/$cm^2$ without damage

Therefore, the operating parameters are between a minimum of 6 Joule/$cm^2$ for pest kill and a maximum of 40 Joule/$cm^2$ to prevent host damage.

The process is operated between these two limits. Host safety and efficient kill are factors to considered. Operating the processor between 10 Joule/$cm^2$ and 30 Joule/$cm^2$ is preferred to effect pest kill without degradation to host. This provides a safety factor of 10 Joule/$cm^2$ and an over minimum pest kill by 4 Joule/$cm^2$.

Process time and throughput are also factors in determining power levels, especially in bulk applications. Higher power levels will have shorter process times but consume more energy. Power conversion efficiency is less of an issue on high value products and of little concern in medical applications. Shorter process times have important applications in medical applications because of energy dissipation to surrounding tissue.

5. Calculate Differential Threshold for Target/Host.

Target: Power required to achieve temperature critical/desired effect $P/A \times t \times (A_\lambda = E_a = m_1 \times C \times (T_c - T_\alpha)$ for host Host: Power to avoid reaching temperature critical/un-desired effect $P/A \times t \times (A) = Ea = m1 \times C \times (Tc - T)$ for target The difference between temperature critical for the host and temperature critical for the target is the differential processing temperature.

The process of the present invention is illustrated further by the following examples.

EXAMPLE 1

Blood Scrubber

A blood scrubber is used to treat blood in order to remove or alter an unwanted component such as a virus, infection, or other component, or to denature a particular type of protein. Blood is diverted out of the body as in a dialysis-type procedure. The blood is then passed through a treatment tube constructed from a substrate having an optical transition of proper wavelength range. Synthetic diamond or some other non-reactive substrate that has transparency at the treatment wavelength is preferably used. High power infrared light or electromagnetic energy is focused on the blood as it passes through the treatment tube. The tube has an optical design that maximizes the absorption in the target matter within the blood as to cause the desired effect. Viruses, bacteria, or other pathogens are targeted.

EXAMPLE 2

Cancer Treatment

Data was acquired between 200 nm and 400 nm. The objective was to identify preliminary structural changes in malignant DNA and compare this to normal DNA through differences in absorption. Differential was noted in three ranges UV-VIS, NIR and Mid IR. A high degree of differential was located at 265 nm with a difference of about eighty times more absorption in malignant DNA. (See FIG. 1) Treatment is not always carried out at the maximum differential in this case at 280 nm. The 265 nm wavelength was chosen over other possible wavelengths due to its low absorption in normal tissue. This is described as the clear path or optimal treatment site. Energy at 265 nm is emitted by appropriate source such as an excimer laser, diode pumped solid state laser, semiconductor laser or flash lamp or other source depending on flux density required per application. Said energy is emitted directly or conveyed to the sight of the lesion and surrounding tissue through fiber optic, a Wave-guide (hollow silica or other substrate,) a light pipe, endoscopes or other conveyance method. Energy will be delivered in sufficient flux density to cause a rapid increase in temperature of the malignant DNA and thereby denature the malignant DNA. DNA is known to denature in a range between about 75° C. and about 90° C. This denaturing or unraveling stops cell divisions and subsequently stops cancer growth. Energy is supplied at high flux density for very short times to cause rapid increase in the temperature of the target DNA without time for heat to dissipate through surrounding tissue. The 265 nm wavelength suggested for use is in the Ultra Violet (UV) range just above the energy of ionization and great care must be taken when working in this range. Exposure to ultraviolet light is a major cause in cancer of the skin in the white population. The action spectrum of carcinogenisis is not completely known. Pathak Invest. Dermatol., (1955) found in experiments on mice that tumors were produced by irradiation with polychromatic radiation between 200-400 nm while no tumors were produced by irradiation with monochromatic radiation at 260 nm, 280 nm, 300 nm, and 360 nm. The dose of monochromatic radiation was three times over those of polychromatic radiation. This information hints at two possible hypotheses, first that skin cancer is a two-photon process or a two-site damage process, where both the chromosome is damaged and the repair mechanism is damaged or disabled. The process described uses only monochromatic radiation that is line locked to ensure single frequency therapy. Frequencies in all ranges above ionization will be considered. Water absorption is a major factor in treating cancer in-vivo. Water absorbs EME in many ranges and must be considered first in frequency selection for this application.

Other substances within malignant cells are also researched for potential differential targets; cell wall, plasma membrane, plasma, proteins, protein of (capsid), polysaccharides, lipids, nucleoid, etc.

$$P/A \times t \times (A_\lambda) = E_a = m_1 \times C \times (T_c = T_\alpha)$$

Flux density calculations for malignant DNA;

Flux density×Time×absorption factor/per-wavelength=Energy absorbed=mass of substance×heat capacity (><=1.2 J/gram° C.)×temp. critical (90° C.)–ambient temp. (37° C.)

EXAMPLE 3

Rice

Figure 3:
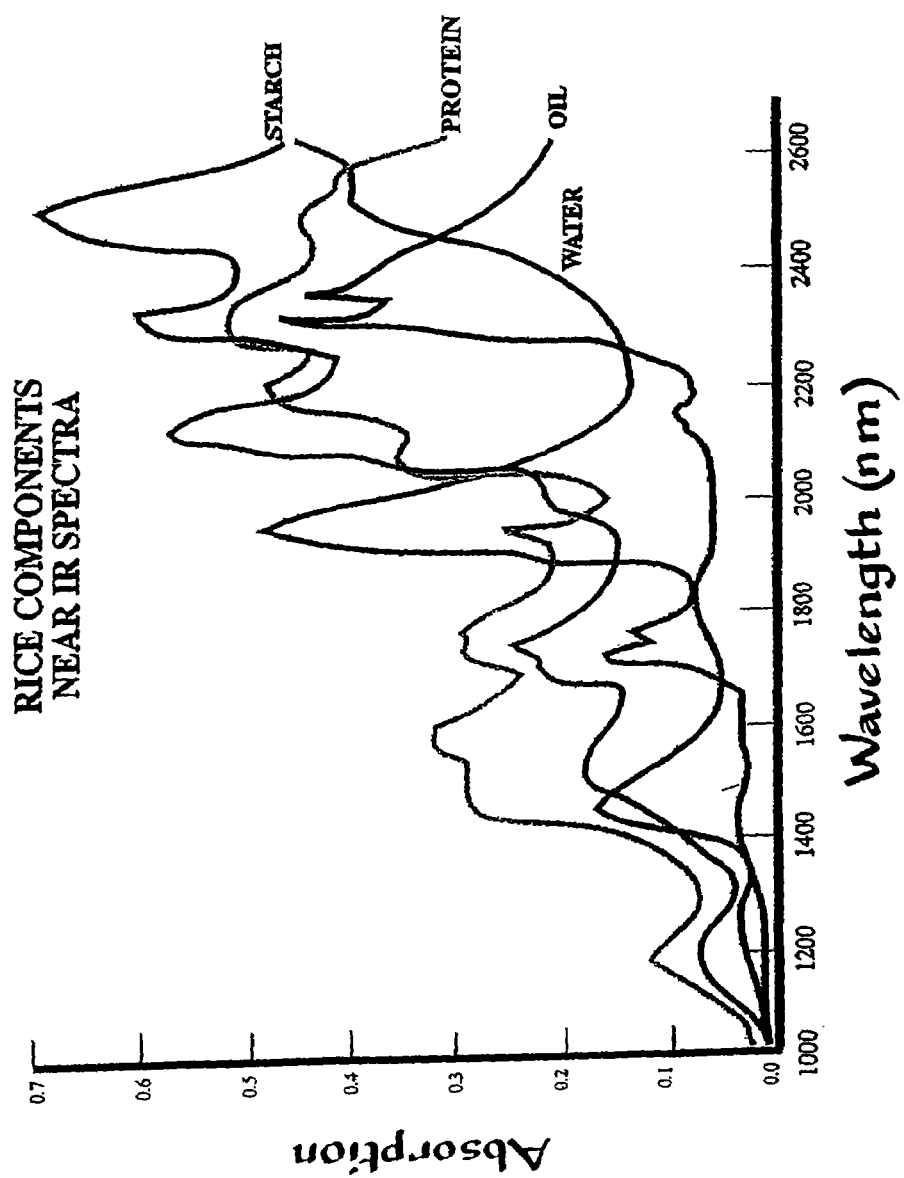
FIG. 3 Near infrared (IR) absorption spectra of rice components.

Rice spectra from 5-10 samples were compared for common absorption peaks. See FIG. 3. Pests that are to be targeted were also evaluated for common absorption peaks. Differential absorption peaks were established. For this application a black body source was chosen.

The black body source was tuned by means of controlling the input power to have a temperature of about 3800° F. This yields an efficiency of about 85% energy conversion.

A black body at 3800° F. has a peak emission at about 1900 nm, matching a combined strong OH bend/stretch absorption peak in pest internal water. The water in rice also has this characteristic peak, but water is a much smaller component of rice. The emission was filtered with a 2000 nm cut off filter to avoid an absorption peak in rice starch and protein. The rice being treated had a water content of about 14%, the pest water content was estimated to be over 75%. Treatment times were from two to ten seconds at a flux density of about ten to twenty watts per sq. inch. The short exposure times coupled with the low water content in rice allowed killing of the pest with little or no effect in the rice. Rice can be conveyed through a treatment zone on a conveyer belt or dropped through a treatment system of baffles or slides to control grain speed during treatment.

In the treatment of rice, one example of a target is lipase enzyme. All types of rice, grains, and nuts can be treated both for disinfection and disinfestations, and to dry the product. The treatment can be applied as the product is received, or before processing, in order to avoid introducing pests into a processing plant. Also, treatment can be applied after milling or processing as well as prior to packaging.

EXAMPLE 4

Agriculture Products

Figure 4:
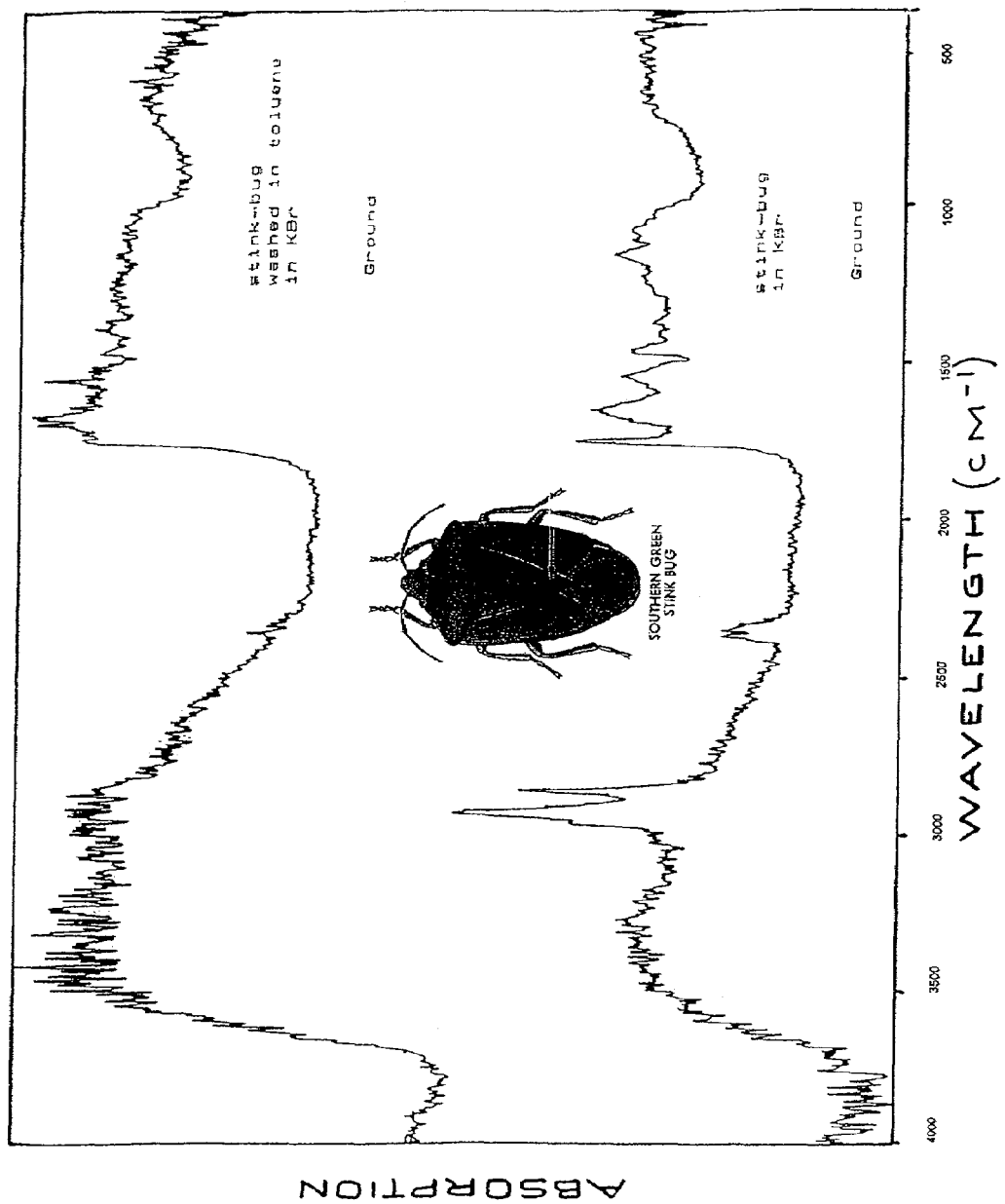
FIG. 4 Absorption spectra of stink bug.

Agriculture and food products with high water content can be treated in much the same manner, but a different component in the pest is preferably targeted. The product is preferably treated at a frequency where the target, pest, or infestation is effected with little to no effect on the host. As described in the section above on arthropods, there are several commonalties in all insects: chitin, wax and water. Wax targeting offers good kill in many pest/products with high water content and in growing plants. FIG. 4 shows two spectra of a stink bug known to vector many diseases harmful to trees and plants. The lower spectra is of the insect's normal absorption, in the upper spectra the wax was removed. The first peaks are in the range between 2900 and 2900 $cm^{-1}$; the second peaks are in the 2300 to 2400 $cm^{-1}$ range; and the third peak falls at about 1750 $cm^{-1}$. The process can be used to create sensory structure difficulties such as targeting of the compound eyes, tympanic membranes, antennae, etc.

Other agricultural products can be treated to denature a targeted protein or enzyme in order to stabilize a product. For example, if the protein responsible for the spoiling of fruit and vegetables is targeted, the shelf life of such products can be increased. Similarly, ground meat can be treated by the process of the invention to destroy *E. coli* bacteria as a target.

EXAMPLE 5

Fleas, Ticks and Lice

Wax and water peaks combined offer a differential pest kill on humans and animals. In this example, fleas on dogs were treated with a black body source having an emission matched to these absorptions peaks. A hand held device was used to expose the subject dog to an infrared source with a peak emission at 1500 nm, and a cut off filter at 750 nm was used to avoid high absorption in the dog. This source was evaluated for use at a wavelength known to be safe for the host, having a peak emission at 1.5 microns which corresponds to a water absorption peak and a fairly high C—H bond absorption at for wax in insects. A flux density of about 0.5 to about 2 watts per sq. inch was used resulting in pest kill and no discomfort to the host. Ticks and lice also are susceptible to this type of treatment. Ticks were killed on human tissue without damage to skin.

EXAMPLE 6

Nematodes

Figure 5:
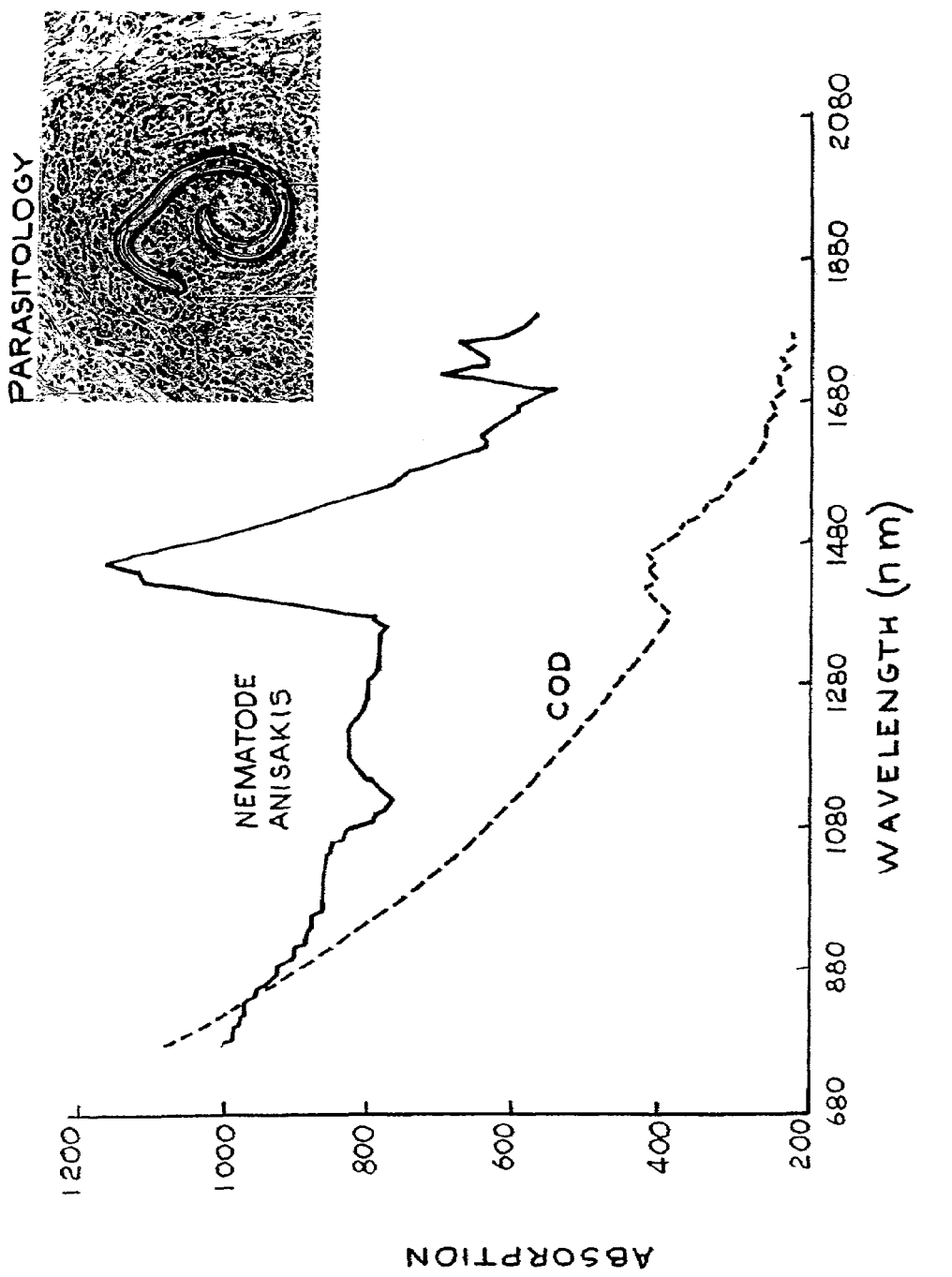
FIG. 5 Absorption spectra of nematode and cod.

Nematodes are often the cause of illness from eating raw fish such as in sushi. Nematodes can be treated in various hosts. FIG. 5 shows spectra in nematode and in cod. Two possible treatment zones or differential peaks are shown. The peak at 1480 nm offers the greatest differential between the cod and the nematode and is considered. The peaks between 1680 nm and 1880 nm also offer ample differential, but also show very low absorption in the host cod, and are therefore preferred in most applications. The 1680 nm to 1880 nm range is preferable because it offers the clearest path for having the least effect on host.

Nematodes also have a devastating effect on many agriculture crops, living in the soil and attacking the roots of crops like strawberries and trees. The soil fumigant methyl bromide is used to kill this pest, but the use of this fumigant will not be allowed after the year 2005 due to its ozone depleting effects. Trials have indicated that control of this pest is possible at wavelengths between 1 mm and 1 megameter, with possible optimization in the kilohertz band.

Soil transmits or is transparent in these ranges allowing penetration of the soil to depths required for treatment. Low power testing disrupted pests in this class at a wavelength of about 3 kilohertz.

EXAMPLE 7

Athlete's Foot

A method for treatment of microorganisms such as athlete's foot and fungus of toenail and skin have been tested. Trials were conducted in which feet of subjects having athlete's foot were soaked in warm water for about ten minutes to hydrate the skin tissue. The feet were then exposed to two treatments of infrared light for about 40 seconds each with a 1500 nm peak energy and a cut-off filter at 750 nm. Treatments on two consecutive days offered control of Athlete's foot with no ill effects to the human host.

EXAMPLE 8

Drying Paint, Glue and Bonding Substances

The drying process for paints, glue, and similar substances requires that the solvents contained in such products be volatized. The differential absorption process can speed up and improve this process. The absorption spectra of the solvents are compared to the components in the paint or glue and the surface they are applied to. Matching applied energy to the solvent and not the pigment or other substances allows much higher energy to be applied without damage to the coated surface or paint or glue.

EXAMPLE 9

Ventilation System

Figure 7:
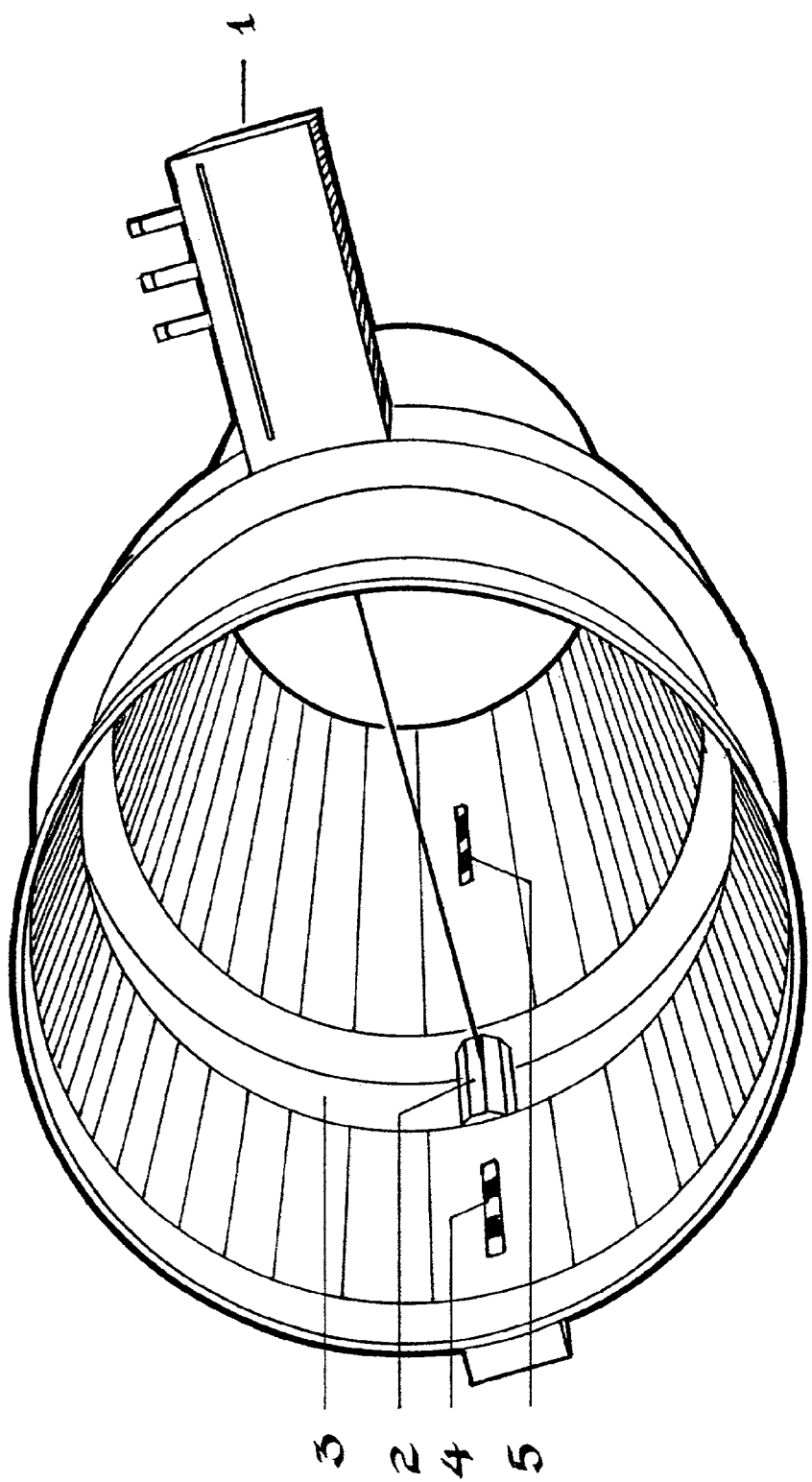
FIG. 7 Ventilation system for disinfesting and disinfecting air.

A ventilation disinfesting/disinfecting system can be used for air treatment to destroy, control or prevent accumulations of airborne pathogens and microbe contamination commonly found in closed ventilation systems including but not limited to spacecraft, submarines, medical facilities, food processing plants, buildings, and hotels. This can be accomplished by sweeping the air stream with high intensity EME matched to the absorption of contaminates contained in the air. A system that utilizes a highly reflective section in air handling system where air flow is subjected to single or multiple wavelength of EME causing undesirable components of air flow to reach temperature critical, while air is not effected or temperature increase is nominal. See FIG. 7. This device provides a platform for treating in high power or low power depending on degree of sterility desired. Air is drawn or pushed through the device and the laser or other source emits energy to kill or vaporize contamination.

Number 1. Emitting Laser Source: Supplies energy. 2. Rotating Mirror: Optimization of flux. 3. Treatment Chamber with High Reflective Surfaces: Concetrates energy. 4. Detectors for Monitoring.

Antiterrorism Modality

The system contains a laser generated high-energy field that incinerates all organic substances as they pass. The process does not disrupt air, its components or significantly increase the air temperature. The sterilization system is designed as a self-contained unit and can adapt easily to any ventilation system.

Organic materials have heat capacities ranging from 1.2 (for solids) to 2.5 (for liquids), joules/gram/degree. This equates to approximately one joule/milligram or one kilowatt/gram required to increase the organic substance temperature to ~500° C., thus combusting the substances.

Energy=mass×heat capacity×the change in temperature $Q = m \times C \times T$ (Joule=watt/second).

(1 kilo watt=1000 joules)

Organic material cannot tolerate a 500° C. environment. All organics combust prior to reaching 500° C. and then contribute energy to the sterilization system upon combustion.

Real-Time Monitoring

In addition to the differential absorption techniques used by our air sterilization system, we have developed a feature as an integral component-real time monitoring and reporting of contaminant levels by type and amount. This provides a significant additional advantage over ultraviolet or other proposed technologies.

Our design incorporates paired sets of monitors, half of each pair on each side of the treatment zone. These monitors detect nitrogen oxides, carbon oxides and water vapor. The differential signal from the paired sets indicates when even small amounts of contaminants are undergoing treatment.

All living organisms contain proteins that produce nitrogen oxides when treated. The carbon detector differential signal reports when organic compounds, such as bacteria, viruses, molds, etc., are present. The nitrogen detectors confirm the presence of these organisms while distinguishing between these organics and non-living sources of carbon, such as carbonate minerals (e.g. chemicals, chalk and most plastics). Because there are differential signals from opposite ends of the treatment zone, ambient levels of impurities, such as varying carbon monoxide levels from nearby vehicles, do not trigger false alarms.

An additional monitor continuously measures the presence and quantity of scattered light and gives a complete picture of contaminant and hazard levels. All of these monitoring techniques are well established and utilize off-the-shelf components. The majority of other previously proposed techniques requires the development of real-time biosensors that have yet to be demonstrated in a laboratory setting, and are certainly suspect in real-world contexts with constantly varying and often unexpected environmental factors.

EXAMPLE 10

Medical Implants and Equipment

The differential absorption process of the present invention can also be used to sterilize and/or remove unwanted contaminants from medical implants and equipment. Silicone is used in a variety of medical implants, such as breast implants. Infection poses a major problem with the use of silicone. Using the process of the present invention, silicone implants can be manufactured and packaged in a material that is transparent to the desired processing wavelength(s). The packaged silicone implant can then be treated to sterilize it before introducing the implant into a patient.

Stainless steel is also commonly used in medical implants. For example, stainless steel is used in artificial joints including artificial knees and hips, and stainless steel pins are often used to fuse joints and bones. One of the problems encountered with the use of stainless steel implants is oil contamination of the steel. Using the process of the present invention, the stainless steel can be treated to remove the contaminating oil before the implant is introduced into a patient.

EXAMPLE 11

Illuminating Tissue or Substance

Illuminating a substance through a process where EME is focused on matter or tissue; human, animal plant, bacterial, viral or chemical at a specific wavelength to cause it to remit energy to aid identification of a specific substance. Applied energy may cause re-emission through defused reflectance, thermal remission (black body emission) or scanned for non-illuminating properties (candling or shadow gram). Tissue can be exposed to specific wavelength of EME to illuminate a substance otherwise undetectable; the tissue can be human, plant etc. Plant tissue like dried fruit is exposed to targeted EME to illuminate and identify pits and pit fragments during processing. Cancer cell may be identifiable through exposing potions of body to specific frequencies of EME that will cause them to heat in a differential manner to locate and identify.

EXAMPLE 11

Illuminating Foreign Material or Substance

Illuminating a substance through a process where EME is focused on matter or tissue; human, animal, plant, bacterial, viral or chemical at a specific wavelength to cause it to re-emit energy to aid in identification of a specific substance. Applied energy may cause re-emission through defused reflectance, reflectance, thermal re-mission (black body emission) or scanned for non-illuminating properties (candling or shadow gram). Tissue can be exposed to specific wavelength of EME to illuminate a substance otherwise undetectable; the tissue can be human or plant. Plant tissue like dried fruit is exposed to targeted EME to illuminate and identify pits and pit fragments during processing. Cancer cell may be identifiable through exposing portions of the body to specific frequencies of EME that will cause them to heat in a differential manner to locate and identify.

EXAMPLE 12

Marking

Marking substances is a group of processes that utilize EME to mark differentially with process-specific frequencies to target infestation or undesirable element of the substance can be changed or excited so it can be referenced or identified. EME can be directed at product causing changes to include but not limited to color change, size change, spectral change etc.

EXAMPLE 13

Tagging or designating a target for attracting a chemical, catalyst, agent, or nanobot. Focusing specific energy at a host in concurrence with some metabolic process or dysfunction to attract a drug or chemical; due to and/or resulting from thermal, physical or other frequency induced reaction. Catalyst and other agents may be concentrated through focused EME. In the future the possibility that nano devices that are designed to repair or perform some task in humans or other substance exciting specific bond sites could potentially direct or attract such devices and others of the future.

EXAMPLE 14

A light-based method or process for conclusively identifying and rejecting pits, twigs, shells and other foreign matter in dried fruit and to package an easier to handle fruit product (less stickiness) without altering the host fruit during high-speed production and packaging. This shall be initially accomplished by defining spectra and deploying EME to treat dried plums immediately prior to packaging then reading the reflected energy or the thermal properties, energy or signal will be processed and used to reject the foreign matter, and will be deployed full scale on packaging lines. This will apply to other dried fruits and vegetables, as well as to fresh fruits, grains, and many other food products.

EXAMPLE 15

A method of treating prostate cancer incorporating an endoscopic device, a delivery system and energy source such as a laser or other source for the proper wavelengths and at the proper power such as to deliver sufficient energy as to cause differential heating of malignant tissue. This device will incorporate hollow, wave-guide fiber optics or focusing optics and remain small enough to enter the rectum. The tissue is very thin between the rectum and the prostate; the bladder is directly behind the prostate from the rectum and the bladder could be filled with reflective fluid to concentrate energy in the prostate.

Although the present invention has been described with reference to preferred embodiments and specific examples, those skilled in the art will recognize that changes can be made in form and detail without departing from the spirit and scope of the invention. As such, it is intended that the foregoing detailed description be regarded as illustrative rather than limiting.

What is claimed is:

1. A method for selectively destroying microbial infestation in a silicone medical implant, said method comprising irradiating said implant with electromagnetic energy at a wavelength at which said energy is absorbed by both said implant and said microbial infestation but absorption of said energy by said microbial infestation exceeds absorption of said energy by said implant by a sufficient differential to destroy said microbial infestation while the amount of said energy absorbed by said implant does not exceed an amount $E_a$ of said electromagnetic energy according to the relation:

$$E_a = m_H \times C \times (T_{H,c} - T_a)$$

in which:

$m_H$ is the mass of the implant,

C is the heat capacity of the implant, $T_{H,c}$ is the critical temperature of the implant, defined as the maximum temperature that the implant can withstand without degradation, and $T_\alpha$ is ambient temperature.

2. The method of claim 1 wherein said electromagnetic energy is in a range selected from the group consisting of ultraviolet-visible, near-infrared, and mid-infrared.

3. The method of claim 1 wherein said electromagnetic energy is in the near-infrared range.

4. The method of claim 1 wherein said electromagnetic energy is obtained from a source selected from the group consisting of an excimer laser, a diode-pumped solid state laser, a semiconductor laser, and a flash lamp.

5. The method of claim 1 comprising irradiating said host with electromagnetic energy optimized by a member selected from the group consisting of filtering, shifting, doubling, Q switching, pulsing, focusing, reflecting, grating, pumping, and accelerating.

6. The method of claim 1 comprising irradiating said implant at an irradiation site and further comprising conveying said implant to said irradiation site by conveying means selected from the group consisting of a conveyor belt, a screw-conveyor, pneumatic conveyance, and a rotating drum.

* * * * *